(12) United States Patent
O'Neil et al.

(10) Patent No.: US 8,182,538 B2
(45) Date of Patent: May 22, 2012

(54) EXPANDABLE FUSION CAGE

(75) Inventors: Michael J. O'Neil, West Barnstable, MA (US); Riley Hawkins, Cumberland, RI (US); Chris Mickiewicz, Bridgewater, MA (US)

(73) Assignee: Depuy Spine, Inc., Raynham, MA (US)

( * ) Notice: Subject to any disclaimer, the term of this patent is extended or adjusted under 35 U.S.C. 154(b) by 1082 days.

(21) Appl. No.: 11/930,576

(22) Filed: Oct. 31, 2007

(65) Prior Publication Data
US 2009/0112319 A1    Apr. 30, 2009

(51) Int. Cl.
*A61F 2/44* (2006.01)
(52) U.S. Cl. .................................. 623/17.16
(58) Field of Classification Search .......... 600/201–246; 606/59, 63, 68, 151–153, 198, 250, 260, 606/278, 279, 326–327; 623/1.15–1.16, 623/17.11–17.16
See application file for complete search history.

(56) References Cited

U.S. PATENT DOCUMENTS

| | | | |
|---|---|---|---|
| 5,125,396 A * | 6/1992 | Ray | 600/208 |
| 6,419,705 B1 * | 7/2002 | Erickson | 623/17.16 |
| 6,500,205 B1 * | 12/2002 | Michelson | 623/17.16 |
| 6,790,233 B2 * | 9/2004 | Brodke et al. | 623/17.11 |
| 6,962,606 B2 * | 11/2005 | Michelson | 623/17.16 |
| 7,018,415 B1 | 3/2006 | McKay | |
| 2001/0034553 A1 | 10/2001 | Michelson | |
| 2002/0143401 A1 | 10/2002 | Michelson | |
| 2004/0199187 A1 * | 10/2004 | Loughran | 606/152 |
| 2005/0021041 A1 | 1/2005 | Michelson | |

* cited by examiner

*Primary Examiner* — Thomas C. Barrett
*Assistant Examiner* — Sameh Boles

(57) ABSTRACT

This invention relates to an expandable intervertebral fusion cage and a method for its use for spinal fusion that reduces annular, vertebral body and cage damage and that is compatible with anterior, posterior as well as minimally invasive surgical techniques.

18 Claims, 16 Drawing Sheets

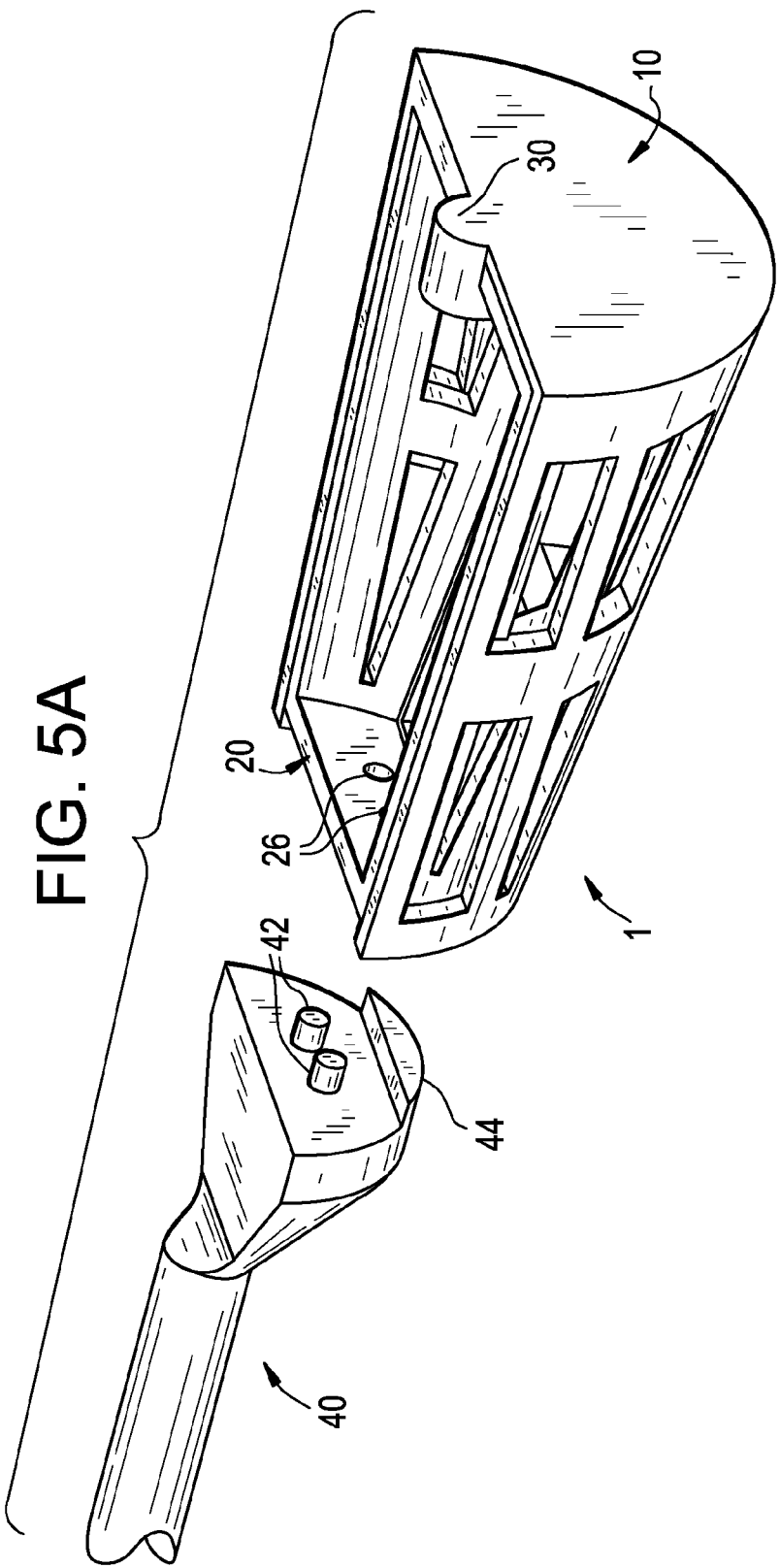

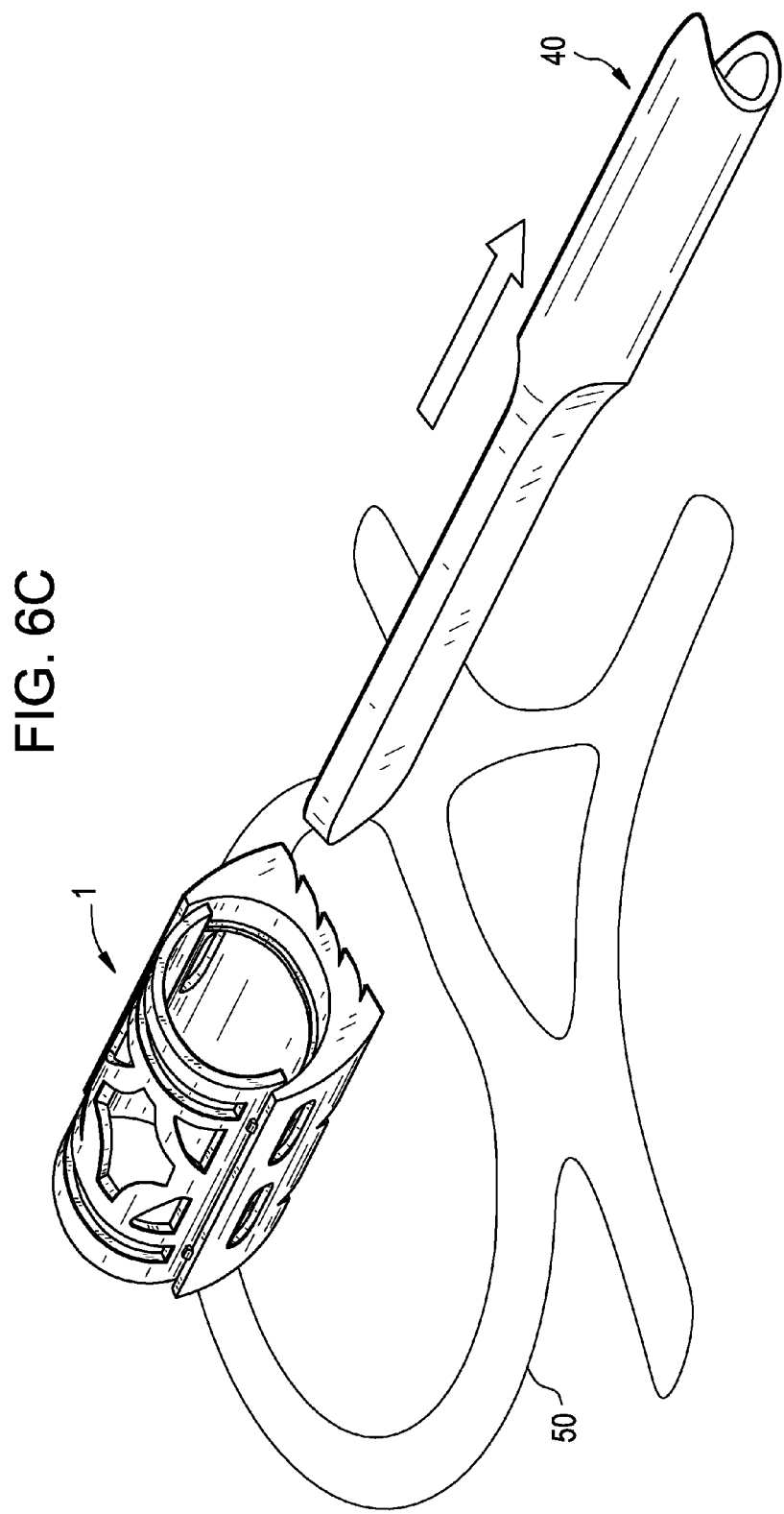

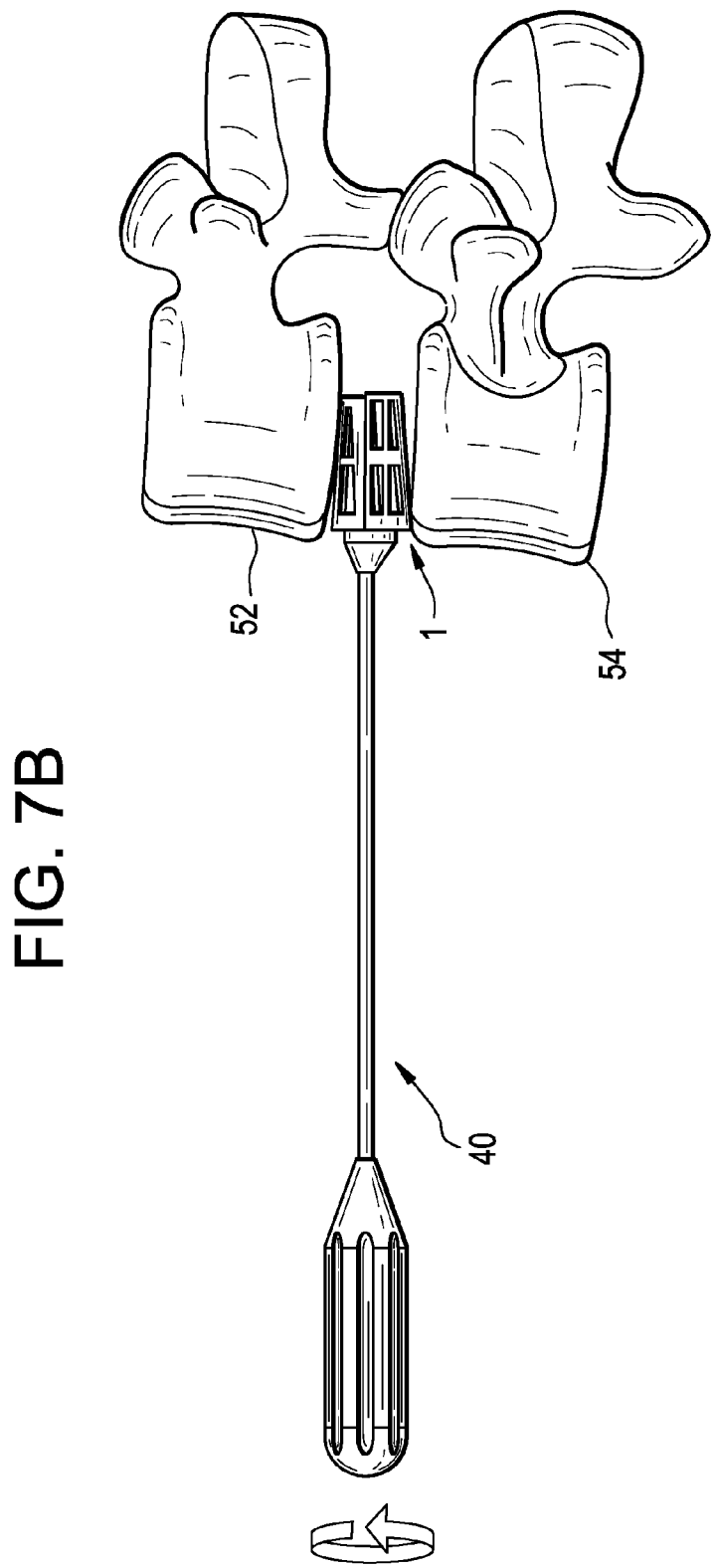

EXPANDABLE FUSION CAGE

BACKGROUND OF THE INVENTION

1. Field of the Invention

This invention is directed toward intervertebral body fusion devices, more particularly to expandable intervertebral body fusion devices.

2. Related Art

Presently, most implanted fusion cages are non-expandable devices although many expandable fusion cage designs are found in the patent literature. The current art discloses jacks, dilators, threaded expanders, cams, pistons and/or packable/inflatable expansion means.

Several challenges exist with currently marketed fixed-form fusion cages if adequate care is not taken during insertion. One challenge is damage to the cage or vertebral body upon insertion into and/or distraction of the intervertebral disc space. Another challenge exists for potential spinal fusion device expulsion when large annular defects are created for insertion of these devices. Yet another challenge is present when over-distraction of vertebral bodies is required to insert fixed-form cages which causes reduction of annular tension as well as soft tissue balance. More specifically, over-distraction is when the intervertebral disc space height is expanded in the axial plane beyond the normal disc space height, stretching the annulus as well as adjacent soft tissues. This results when a non-expandable/fixed form lordotic cage(s) are inserted into the disc space from the posterior or posterior lateral direction. The lordotic angle on the cage creates an anterior disc space height that is larger then the posterior disc space height. The disc space is expanded (or over distracted) to the larger anterior height in order to insert a intervertebral device into the disc space. This overdistraction reduces compressive forces on the cage following insertion. Therefore, it would be advantageous to provide an intervertebral disc cage that does not cause overdistraction of the disc space.

A fair portion of the art in expandable interbody fusion devices are related to cylindrical or conical devices.

US 2005/0021041 and US 2002/0143401 relate to interbody fusion implants that are radially expandable at one of the leading or trailing ends to expand both the height and the width of the implant. US 2002/0107574 is directed toward an expandable intervertebral having a rod for insertion into a tapered bore of an implant to expand the distance between the top portion and bottom portion of the implant. US 2001/0034553 is related to a push-in interbody spinal fusion implant having expandable height and having a frusto-conical shape or shape of cylinder split along a horizontal plane through its mid-longitudinal axis with an upper member and a lower member angled to each other during insertion into the spine. U.S. Pat. No. 7,018,415 is directed to an expandable intervertebral disc space implant having an expansion member such as a cam or rack and pinion.

This invention differs from prior art because it employs a non-disclosed expansion means to increase disc height. This means is the rotation of the inner cylindrical or conical axially nested endplate within the outer endplate. Historical art utilizes jacks, dilators, threaded expanders, cams, pistons and/or packable/inflatable expansion means.

BRIEF DESCRIPTION OF THE DRAWINGS

FIGS. 5A-C depict steps in deploying the device of FIGS. 3A-C with an inserter.

FIGS. 6A-C depict steps in deploying the device of FIGS. 2A-C in a posterior spine application.

FIGS. 7A-C depict steps in deploying the devices of FIGS. 3A-C in an anterior spine application.

SUMMARY OF THE INVENTION

One embodiment of this invention relates to an intervertebral body implant comprising:
a) a first shell; and
b) a second shell;
wherein the first shell and the second shell are coaxially aligned and rotatable from a first position to a second position wherein in the first position, the first shell is received within the second shell, and wherein in the second position, the first shell rotates substantially out of the second shell to form a closed implant.

A further embodiment of this invention relates to a method of disc space distraction comprising the steps of:
a) providing an intervertebral body implant comprising:
   (i) a first shell; and
   (ii) a second shell, wherein the first shell and the second shell are coaxially aligned and rotatable from a first position to a second position wherein in the first position, the first shell is received within the second shell, and wherein in the second position, the first shell substantially rotates out of the second shell to form a closed implant;
b) providing an intervertebral body implant inserter and attaching the inserter to one or the other of the first shell or second shell of the implant; and
c) rotating the inserter and the corresponding shell that the inserter is attached with from the first position to the second position, whereby the act of rotating the shell distracts the intervertebral disc space through rotation of the inserter and the corresponding rotation of the attached shell to provide an implant in the second, closed position.

DETAILED DESCRIPTION OF PREFERRED EMBODIMENTS OF THE INVENTION

In general, this invention it related to a device having two or more largely cylindrical, conical, wedge-like, or frusto-conical halves or portions (i.e., shells) that are axially nested. The device in its open position or first position, i.e., nested, is inserted into the disc space and rotated so that the inner shell rotates out of the outer shell to a second position or closed position to form a closed shell. Thus, the overall height of the device from the nested or open position is approximately one half that of the final device height in the closed position.

The inner shell of the device(s) is rotated by several methods to expand the height and provide appropriate lordosis or kyphosis. The devices are generally hollow to provide for filling with varying osteogenic fillers and generally porous to allow for graft filling, bony ingrowth and spinal fusion. Thus, rotation of the inner shell of the device from the outer shell of the device forces intervertebral disc expansion to regain disc height, spinal alignment and stability.

Figure 1A:
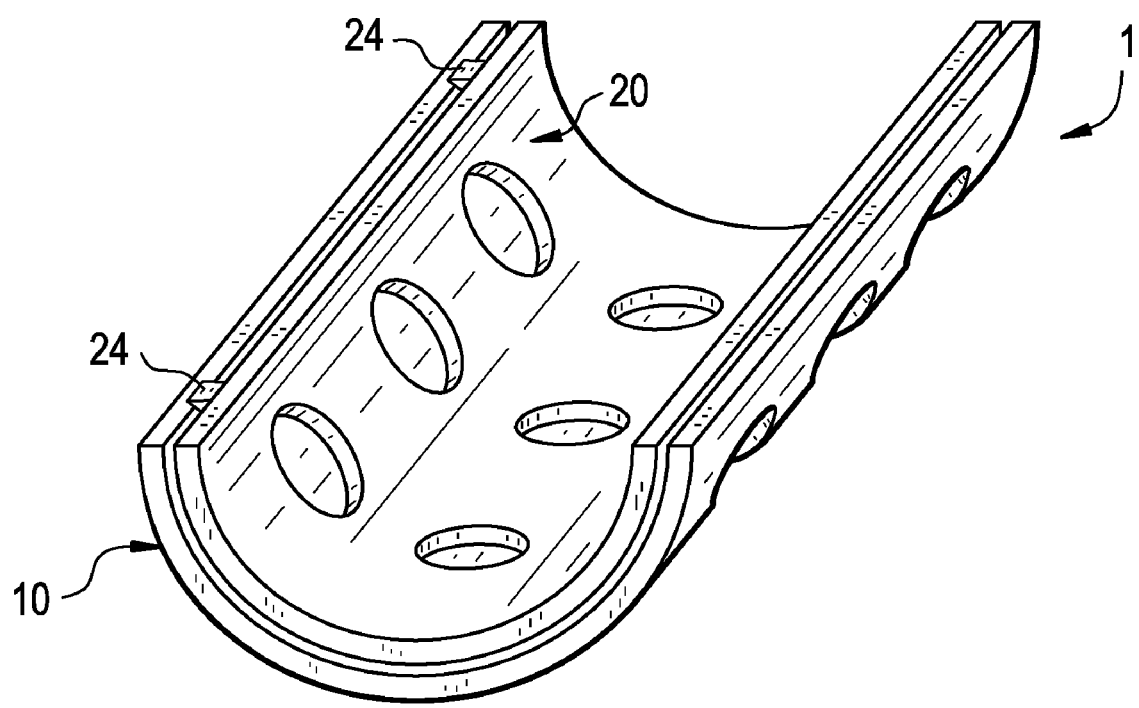
FIGS. 1A-D depict a cylindrical embodiment of this invention.
Figure 1B:
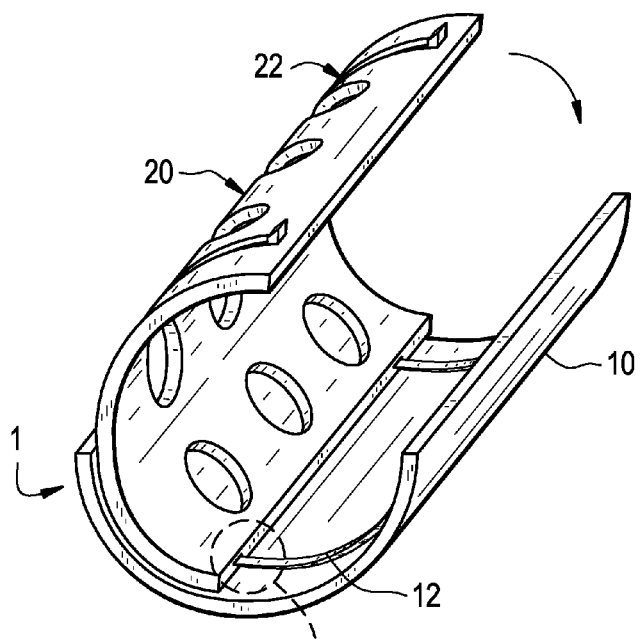
Figure 1C:
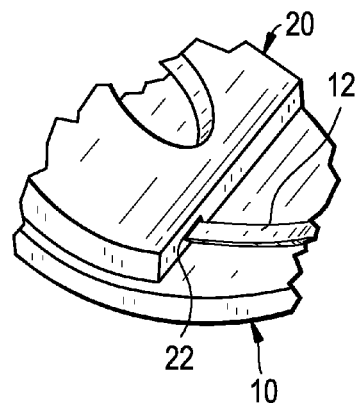
Figure 1D:
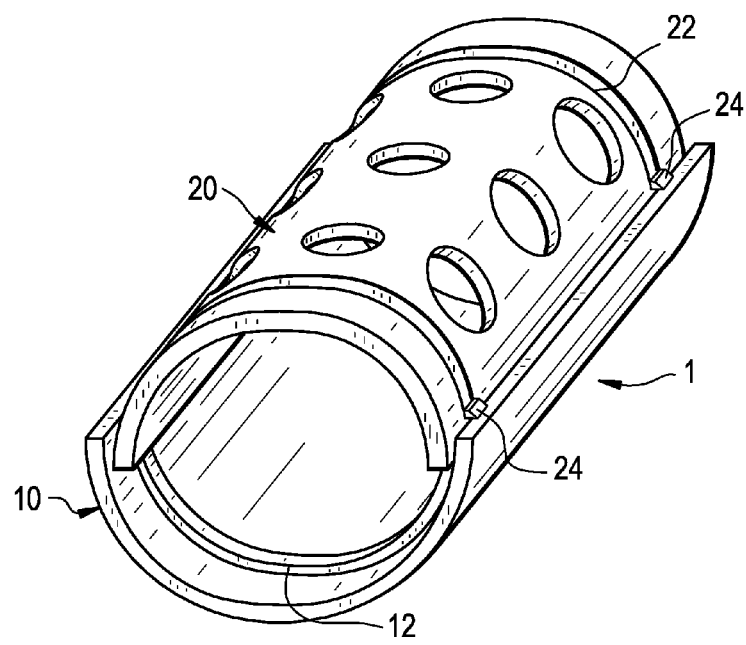

FIGS. 1A-1D depict several features of a cylindrical embodiment of the device of this invention. In FIG. 1A, device 1 is shown comprising an outer or first shell 10 and an inner or nested shell 20. Stops 24 are shown attached to shell 20 and are used to prevent shell 20 from over rotating past or into shell 10. FIG. 1B depicts device 1 rotated to a semi-closed position and further depicts rails 12 and receivers 22. The function of rails 12 and receivers 22 is to guide and secure shell 20 as it rotates out of shell 10 to its final closed position as shown in FIG. 1D. FIG. 1C depicts one embodiment for how rail 12 is engaged with receiver 22. In this instance, the shape of receiver 22 is that of an inverted triangle into which rail 12 (also in complementary inverted triangle form to receiver 22) is received. Additionally, a pin and corresponding and complementary slot within the opposing shell may be used. It should be noted that many other type of rail/receiver geometries may be employed to secure and guide shell 20 with respect to shell 10. Some of these geometries include T-shaped, L-shaped, V-shaped, J-shaped, C-shaped, and box shaped geometries. FIGS. 1A-C also depict openings or apertures in the surface of shells 20 and 10, to allow for bone ingrowth.

Figure 2A:
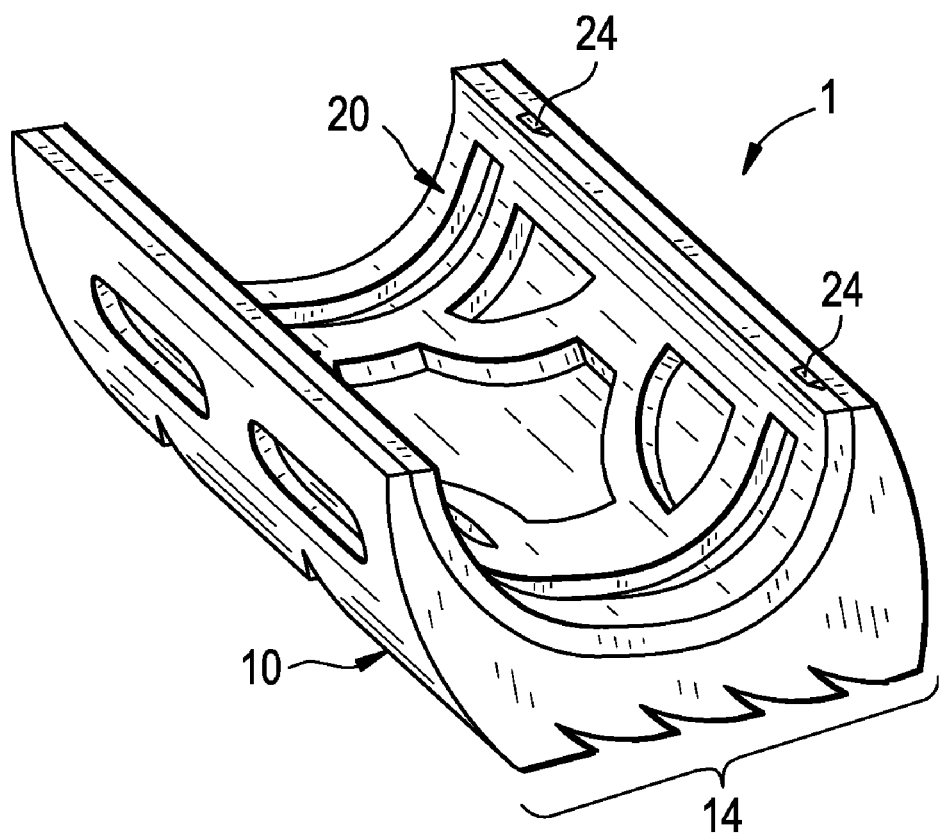
FIGS. 2A-C depicts another cylindrical embodiment of this invention with a bottom portion adapted to lie flush with a bone interface.
Figure 2B:
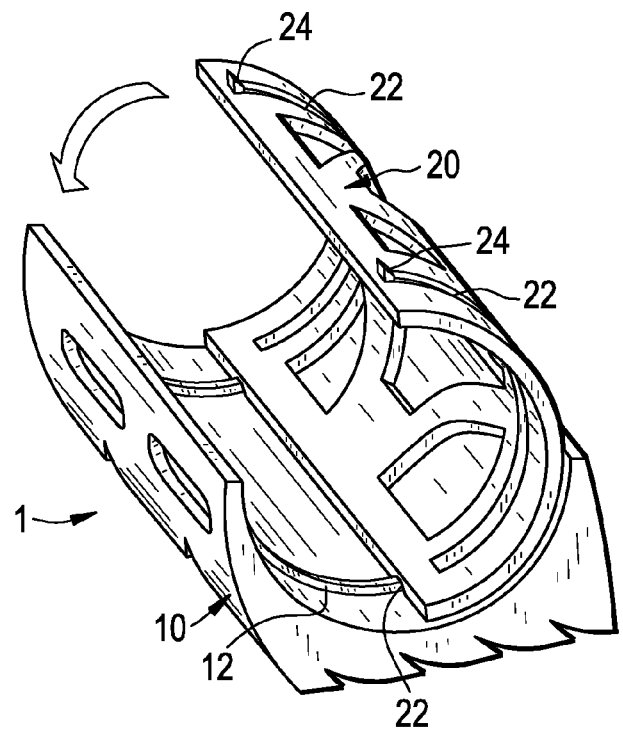
Figure 2C:
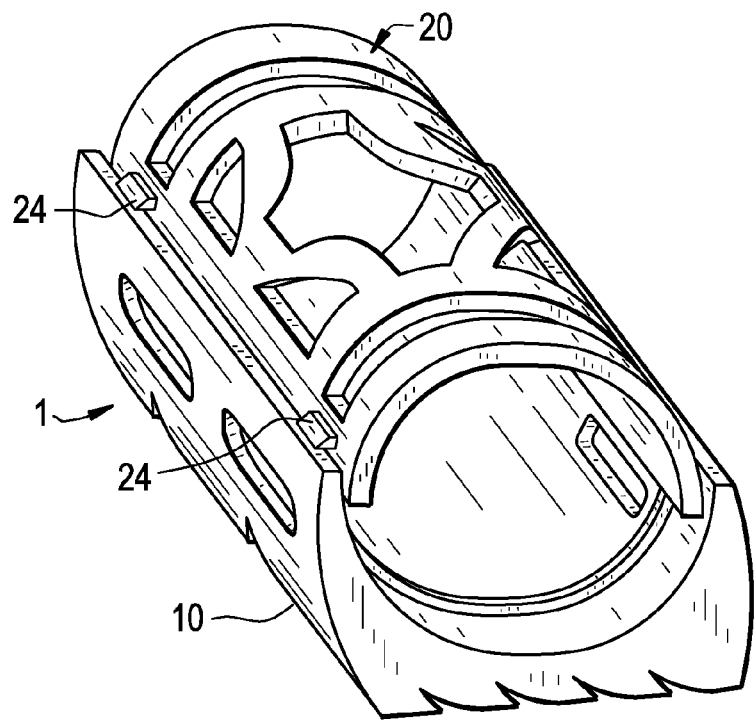

FIGS. 2A-C depict yet another embodiment of a cylindrical form of device 1. In this instance shell 20 is rotated counter-clockwise out of shell 10. Furthermore, device 1 contains a flattened, and optionally textured or modified, surface 14 designed to allow device 1 to rest flatly and securely with respect to its inserted position on a bone such as the top surface of an intervertebral body. Suitable texturing of surface 14 can comprise projecting spikes, barbs, fins, teeth and ribs, and other implant attachment features known to those of skill in the art. FIGS. 2A-C also depict openings or apertures in the surface of shells 20 and 10, to allow for bone growth into and through the cage.

Figure 3A:
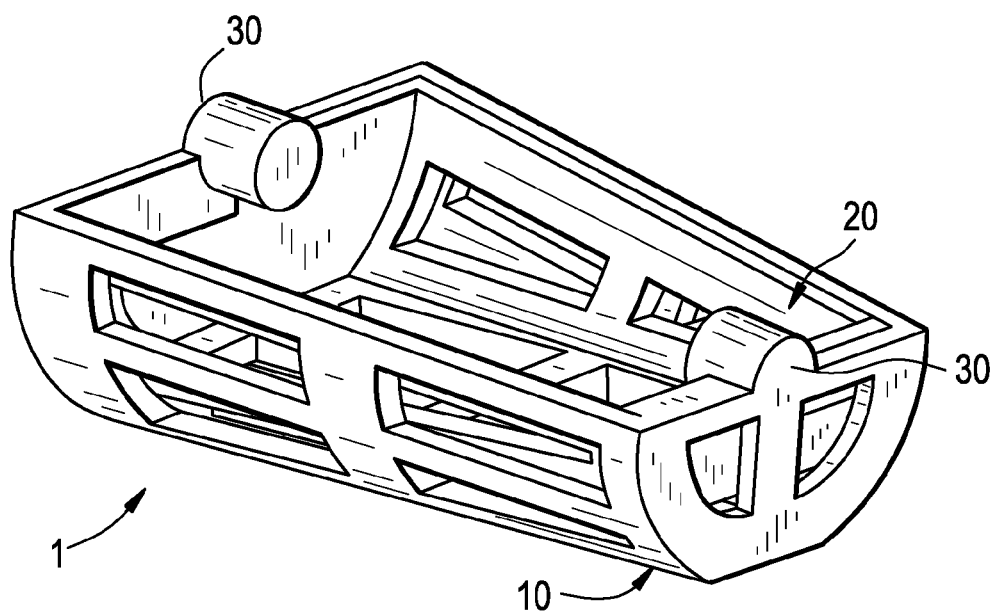
FIGS. 3A-C depict a wedge shaped embodiment of this invention.
Figure 3B:
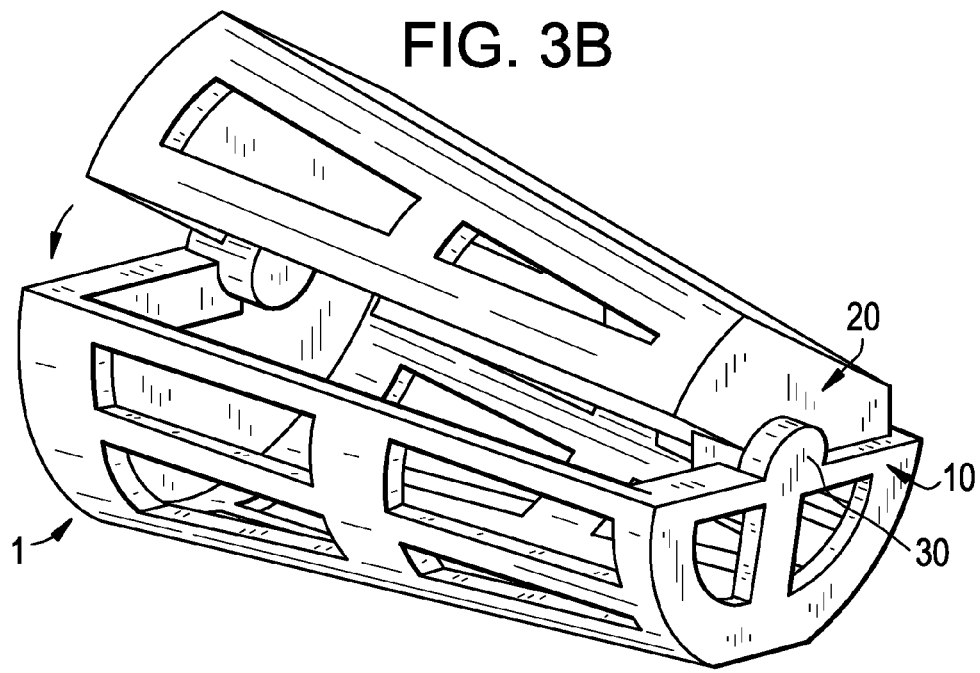
Figure 3C:
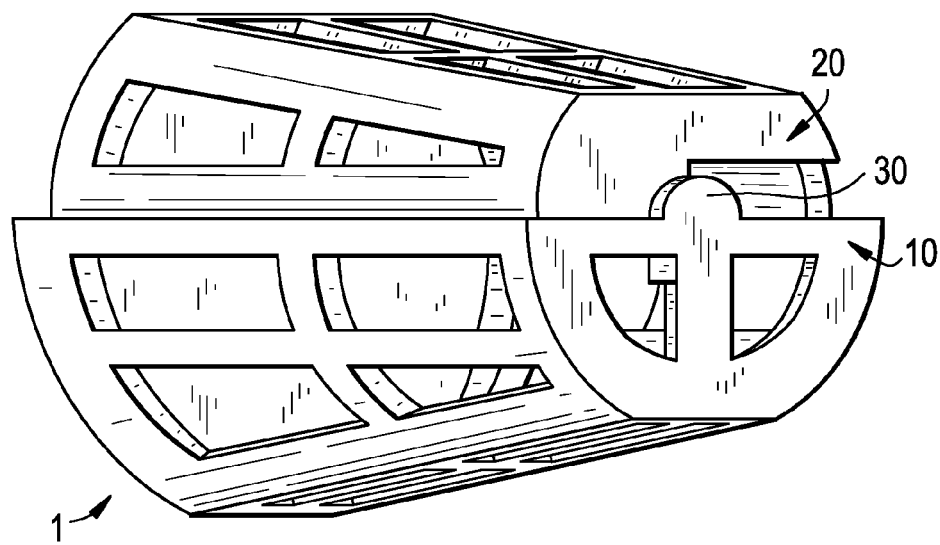

FIGS. 3A-C show a wedge-shaped form of device 1. In this embodiment, shell 20 rotates out of shell 10 through pivot points 30 which comprise a pin and receiver. In this embodiment the receiver is shown on the inner surface of shell 10, while the pin (not shown in detail) is on the outer surface of shell 20. These pin receiver pairs are axially located at the center point of the respective proximal and distal ends of device 1. FIG. 3B shows device 1 in a semi-closed position, while FIG. 3C shows device 1 in the closed position.

Figure 4A:
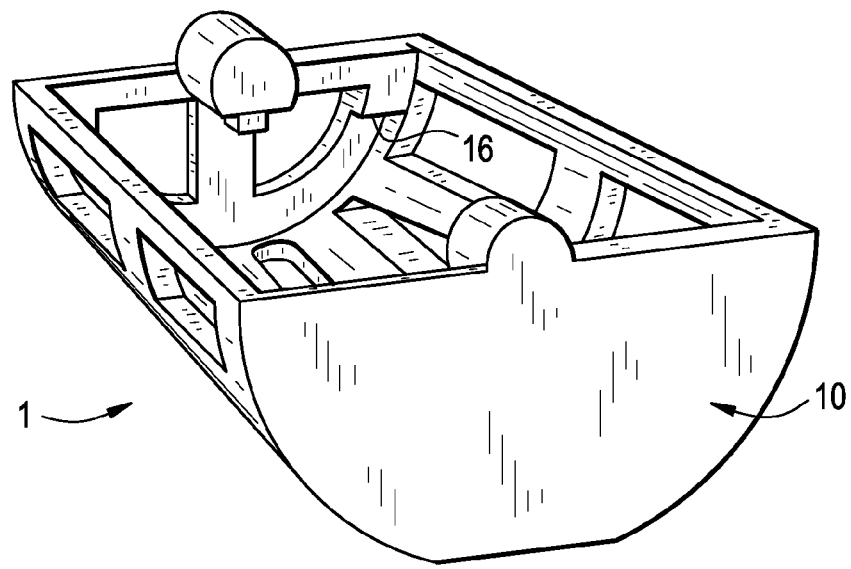
FIGS. 4A-B depict additional optional features of the embodiment of FIGS. 3A-C.
Figure 4B:
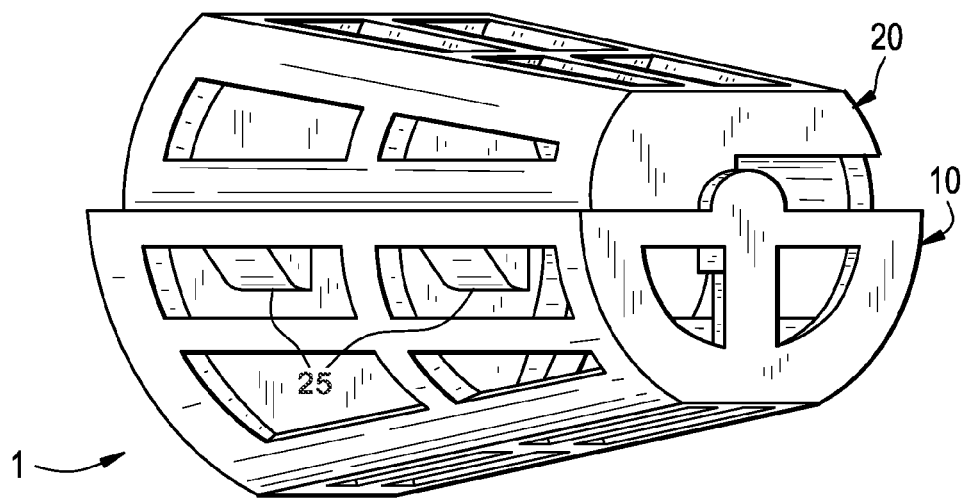

FIGS. 4A and 4B show additional and optional features of device 1 as depicted in FIGS. 3A-C. FIG. 4A shows feature 16 which functions to prevent shell 20 from over rotating into shell 10. FIG. 4B shows snaps 25 which function to lock shell 20 relative to shell 10. Snaps 25 are integral to shell 20 and lock into receiving points of shell 10. Snaps 25 are integral to shell 20 and lock into receiving points of shell 10. Snaps 24 are integral to shell 20 and lock into receiving points of shell 10.

Figure 5B:
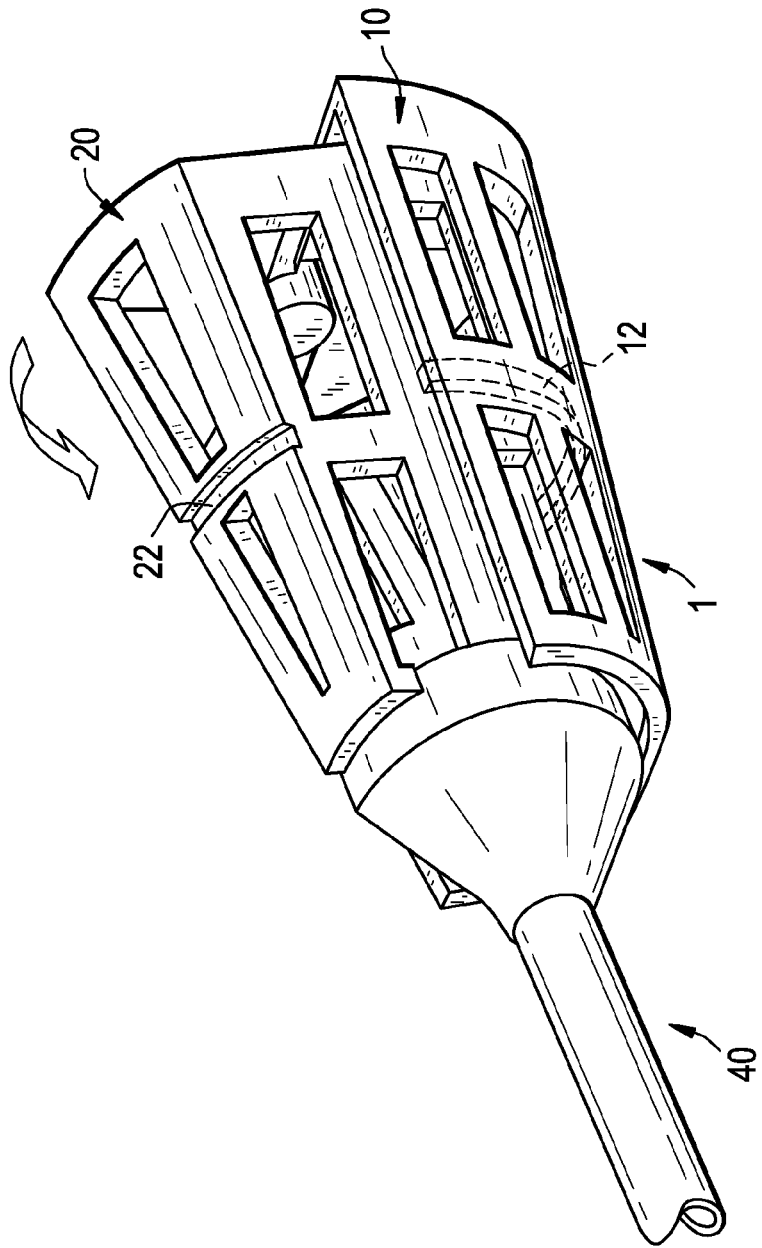
Figure 5C:
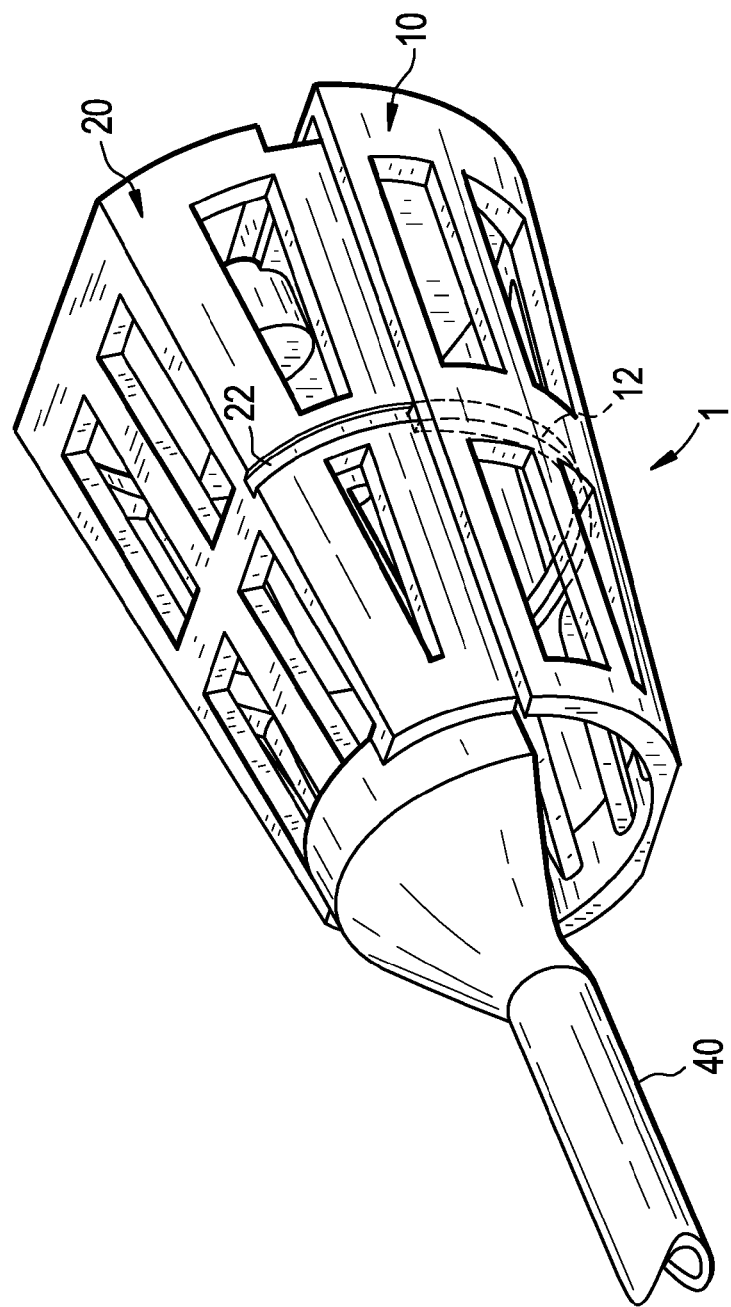

FIGS. 5A-C show use of wedged-shaped device 1 as it is used in conjunction with inserter 40. In FIG. 5A the distal end of inserter 40 provides projections 42 which engage apertures 26 of shell 20. Also depicted at the distal end of inserter 40 is shelf 44 which engages shell 20 (not shown). It should be noted that other engagement features may be used by one skilled in the art and FIG. 5A merely shows one possible engagement embodiment. FIG. 5B shows inserter 40 engaged with device 1 as shell 20 is rotated counter-clockwise from shell 10. Rotation of shell 10 out of shell 20 is accomplished by used of the pivot point 30 (identified in FIG. 5A) and receiver 22 and rail 12. The geometry of receiver 22 and rail 12 may be the same or similar to that shown in FIG. 1C or it may be any other suitable geometry as discussed above regarding FIG. 1C. Finally, FIG. 5C shows device 1 in the closed position.

Figure 6A:
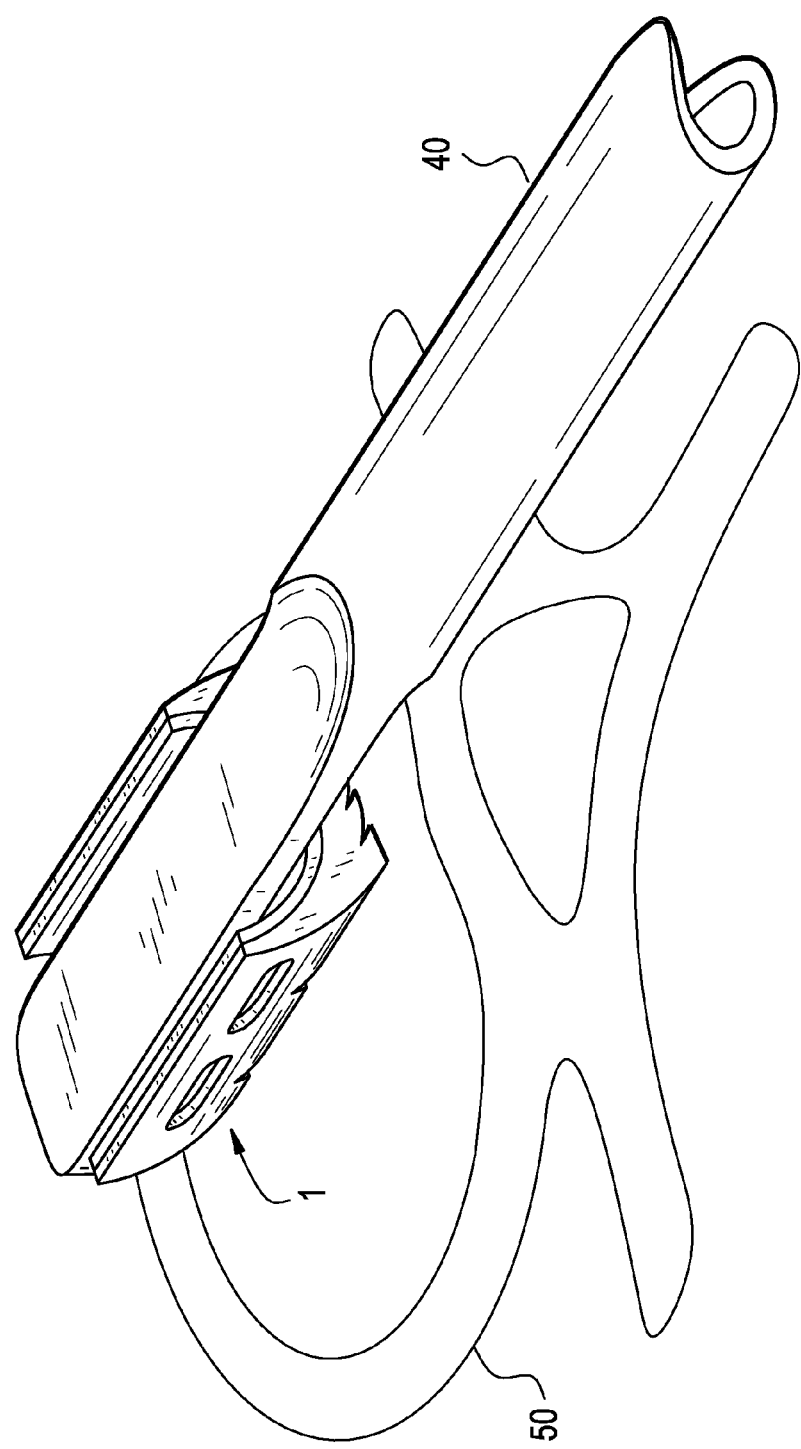
Figure 6B:
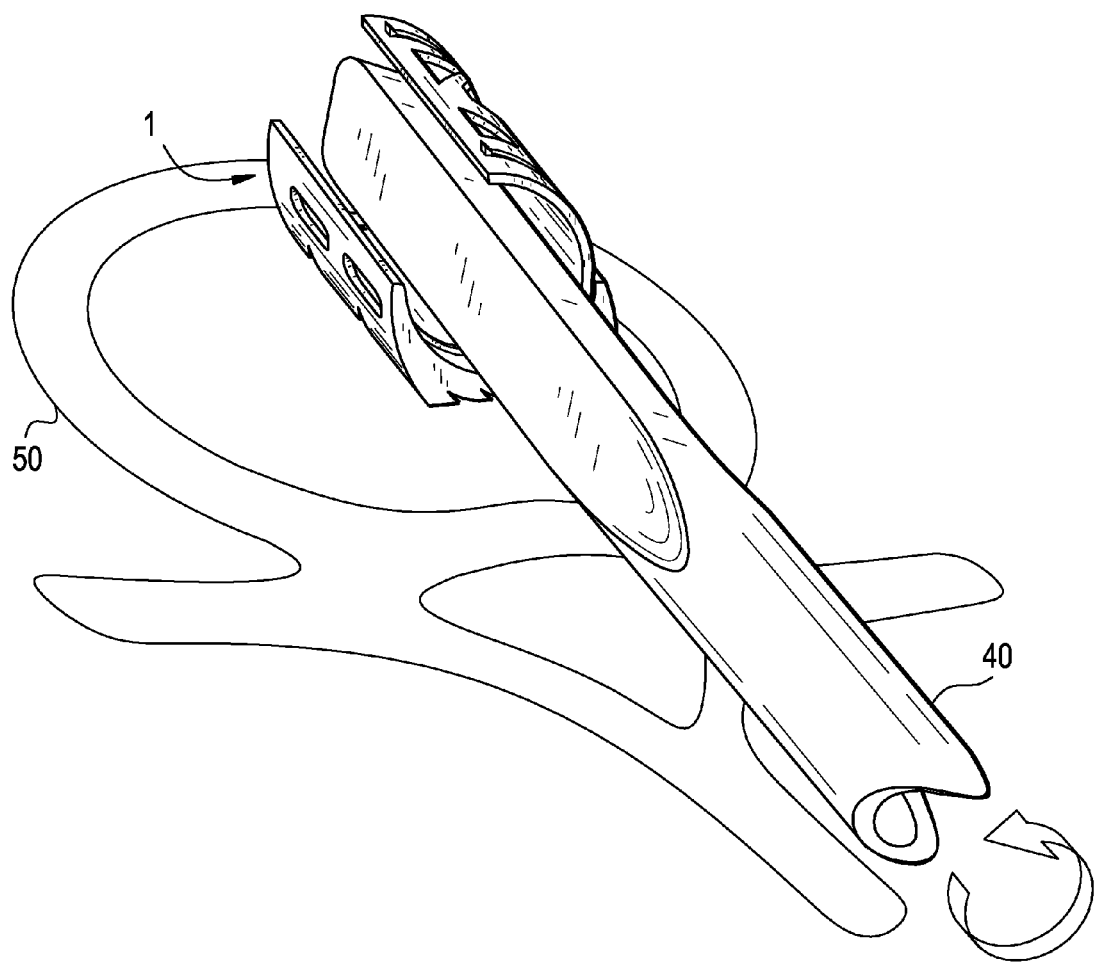

FIGS. 6A-C show further embodiments for posterior spinal insertion using device 1 as depicted in FIGS. 2A-C. Specifically, FIG. 6A shows device 1 engaged with inserter 40 as vertebral body 50 is approached from the posterior position. FIG. 6B further shows counter-clockwise rotation of the inner shell of device 1. Finally, FIG. 6C depicts device 1 in the closed position with inserter 40 being withdrawn. It should be noted that inserter 40 in this embodiment is of a simple "popsicle stick" design which is merely designed to engage and rotate the inner shell of device 1. It should be noted that one skilled in the art would be able to design other means for attaching inserter 40 to device 1 without departing from the spirit of this invention.

Figure 7A:
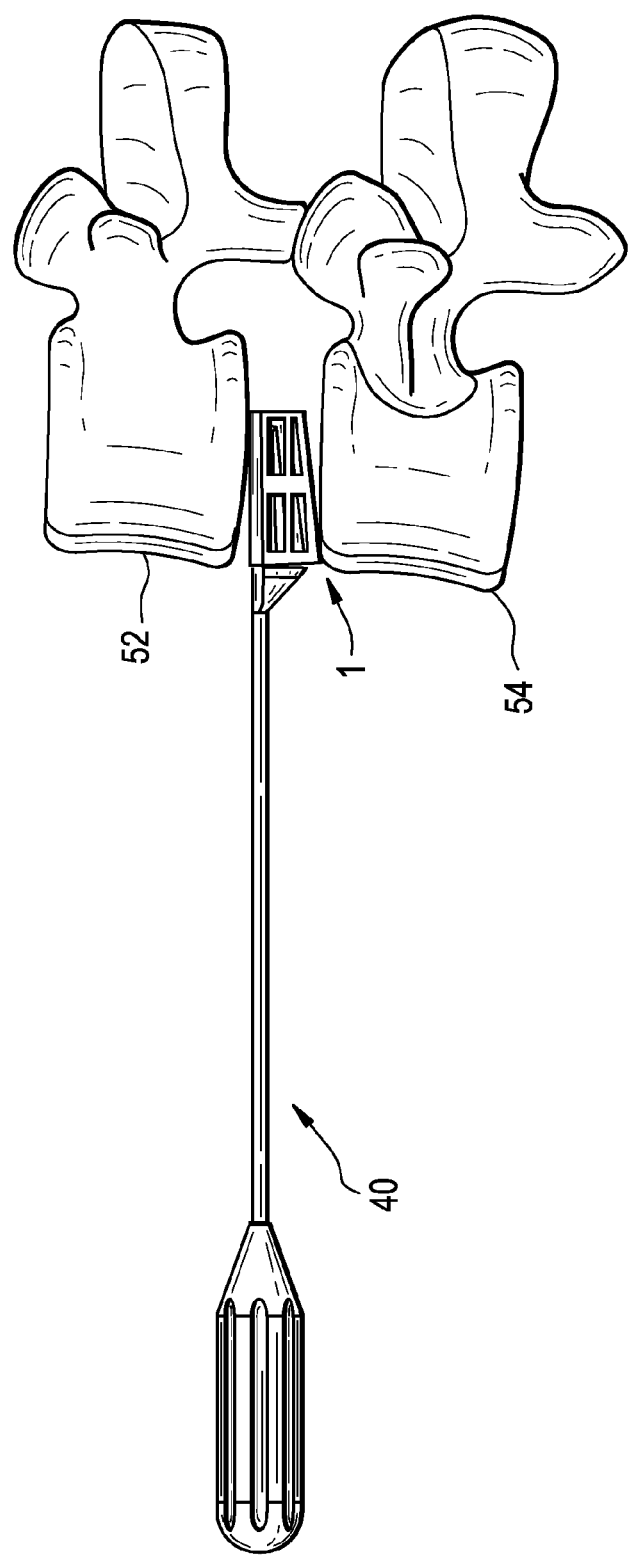
Figure 7C:
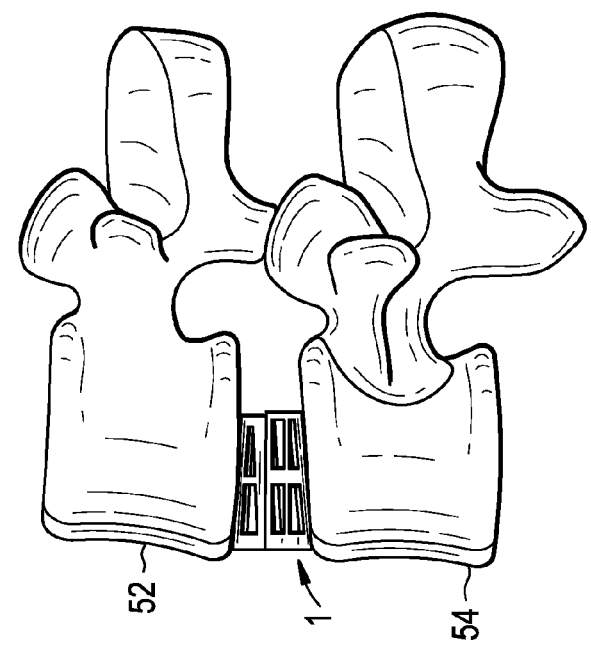
Figure 7C:
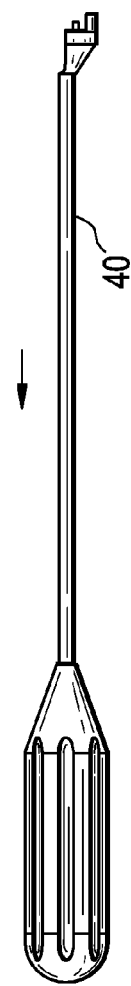

FIGS. 7A-C show yet another deployment of a wedged-shaped device 1 of this invention in anterior deployment between vertebral bodies 52 and 54. More specifically, FIG. 7A shows device 1 attached to inserter 40 in the anterior approach to vertebral bodies 52 and 54. FIG. 7B depicts device 1 being rotated in a counter-clockwise position and FIG. 7C shows device 1 resting between vertebral bodies 52 and 54 with inserter 40 being withdrawn.

In all embodiments, the devices may be implanted by insertion methods to deploy the devices in the anterior or posterior positions. Also, while the foregoing descriptions relate to the inner shell rotating out of the outer shell, it should be noted that in some instances it may be desired to rotate the outer shell around the inner shell in order to accomplish expansion of the device and distraction of the vertebral bodies. It should also be noted that the direction of rotation of the shells can be either counter-clockwise or clockwise.

Lordosis, kyphosis and/or coronal or sagittal radius of curvatures can be included on the surfaces of the devices of this invention as required to improve form and fit the vertebral bodies.

The device of this invention may be comprised of materials typical of intervertebral fusion cages including titanium such as $TiAl_6V_4$, stainless steel (SS), polyketones such polyetheretherketone (PEEK), cobalt alloys such as cobalt chromium (CoCr), resorbable polymers such as polylactic acid (PLA) and polyglycolic acid (PGA), for example. Porous areas or open surfaces can be fabricated in each of the nested cylindrical or frustoconical shells to allow for bony ingrowth and fusion. The hollow area between the rotated cylindrical or frustoconical devices can be filled by injection, insertion or packing with many and any osteogenic or inductive materials including bone, bone substitutes (Conduit, Conduit R, Vitos, HEALOS® for example), growth factors, (BMP's, rhGDF-5) or can be filled with a prefabricated hybrid polymer containing osteoinductive/conductive agents as well as growth factors, anti-inflammatory or analgesics for elution at desired rates. Additionally, the surfaces or at least of portion of the surfaces (i.e., the shells of the device) of the device may be coated or impregnated with osteoinductive/conductive agents such as hydroxy appetite (HA) and tricalcium phosphate (TCP) as well as growth factors, anti-inflammatory or analgesics for elution at desired rates.

A further embodiment of this invention relates to a method of disc space distraction comprising the steps of:
   a) providing an intervertebral body implant comprising:
      (i) a first shell; and
      (ii) a second shell, wherein the first shell and the second shell are coaxially aligned and rotatable from a first position to a second position wherein in the first position, the first shell is received within the second shell, and wherein in the second position, the first shell substantially rotates out of the second shell to form a closed implant;

b) providing an intervertebral body implant inserter and attaching the inserter to one or the other of the first shell or second shell of the implant; and c) rotating the inserter and the corresponding shell that the inserter is attached with from the first position to the second position, whereby the act of rotating the shell distracts the intervertebral disc space through rotation of the inserter and the corresponding rotation of the attached shell to provide an implant in the second, closed position.

It should be noted that the intervertebral disc space comprises the space between the vertebral bodies that results from the full or partial removal of an intervertebral disc.

It should be understood that the foregoing disclosure and description of the present invention are illustrative and explanatory thereof and various changes in the size, shape and materials as well as in the description of the preferred embodiment may be made without departing from the spirit of the invention.

What is claimed is:

1. An intervertebral body implant comprising: a first shell having an inner surface and an outer surface, and a pin protruding from the outer surface of the first shell; and a second shell having an inner surface and an outer surface, the inner surface of the second shell having a receiver formed therein; wherein the first shell and the second shell are coaxially aligned and rotatable from a first open position to a second closed position about the pin; wherein in the first position, the first shell is received within the second shell, and wherein in the second position, the first shell substantially rotates out of the second shell to form a closed implant, and wherein the pin is located so as to engage the receiver.

2. The intervertebral body implant of claim 1, wherein the first shell and second shell form a frusto-conical shape in the second position.

3. The intervertebral body implant of claim 1, wherein the first shell and second shell form a wedge shape in the second position.

4. The intervertebral body implant of claim 1, wherein the implant comprises two pin and receiver pairs, one pin and receiver pair positioned at center point of implant's proximal end and the second pin and receiver pair positioned at center point of implant's distal end.

5. The intervertebral implant of claim 1 wherein the second shell has an outer surface which is modified to lay flat on vertebral body it will be positioned on.

6. The intervertebral implant of claim 1, wherein the second shell has a flat outer surface textured to engage vertebral body.

7. The intervertebral implant of claim 1, wherein at least a portion of the inner or outer shells' surfaces are porous to allow bony growth onto and through.

8. The intervertebral implant of claim 1, wherein at least a portion of the inner or the outer shells' surfaces are coated with an osteoinductive or osteoconductive agent to allow bony growth onto the cage.

9. The intervertebral body implant of claim 1, wherein the first shell has at least one of a proximal end wall extending from the inner surface and a distal end wall extending from the inner surface, and the pin extends from at least one of the proximal end wall and the distal end wall.

10. An intervertebral body implant comprising:
a first shell comprising an outer surface, an inner surface, the inner surface being substantially arcuate, a proximal end extending substantially perpendicularly from the inner surface, and a distal end spaced apart from the proximal end and extending substantially perpendicularly from the inner surface;
a second shell comprising a substantially arcuate outer surface shaped to be at least partially received within the inner surface of the first shell;
wherein the first shell and the second shell are coaxially aligned and rotatable from a first position to a second position wherein in the first position, the outer surface of the first shell is adjacent the inner surface of the second shell, and wherein in the second position, the first shell substantially rotates out of the second shell to form a substantially closed implant.

11. The intervertebral body implant of claim 10, wherein the second shell comprises a proximal end extending substantially perpendicularly from the inner surface, and a distal end spaced apart from the proximal end and extending substantially perpendicularly from the inner surface.

12. The intervertebral body implant of claim 10, wherein at least a portion of the outer surface of first shell is flat.

13. The intervertebral body implant of claim 10, wherein at least a portion of the outer surface of second shell is flat.

14. An intervertebral body implant comprising: a first shell having an inner surface and an outer surface, the outer surface of the first shell having a receiver formed therein, the receiver extending circumferentially; a second shell having an inner surface and an outer surface, and a rail protruding from the inner surface of the second shell, the rail extending circumferentially; wherein the first shell and the second shell are coaxially aligned and rotatable from a first position to a second position wherein in the first position, the first shell is substantially received within the second shell, and wherein in the second position, the first shell substantially rotates out of the second shell to form a closed implant; and wherein rail of the second shell engages the receiver of the first shell over an arc greater than 10 degrees.

15. The intervertebral body implant of claim 14, wherein the first shell and second shell are cylindrical in shape.

16. The intervertebral body implant of claim 14, wherein the first shell is engaged with the second shell by the receiver and rail.

17. The intervertebral body implant of claim 16 wherein the geometry of the receiver and the rail are of complementary inverted triangles.

18. The intervertebral body implant of claim 16 wherein the geometry of the receiver and the rail are of complementary T-shapes.

* * * * *